United States Patent [19]
Chan et al.

[11] Patent Number: 5,270,049
[45] Date of Patent: Dec. 14, 1993

[54] 2-DECARBOXYL-2-AMINOALKYL-PROSTA-GLANDINS AS OCULAR HYPOTENSIVES

[75] Inventors: Ming F. Chan, Lake Bluff, Ill.; David F. Woodward, El Toro, Calif.

[73] Assignee: Allergan, Inc., Irvine, Calif.

[21] Appl. No.: 611,029

[22] Filed: Nov. 9, 1990

[51] Int. Cl.$^5$ .................. A61K 31/557; A61K 31/765
[52] U.S. Cl. .................................... 424/427; 514/573; 514/530
[58] Field of Search ............ 514/530, 573, 9.3; 424/427

[56] References Cited

U.S. PATENT DOCUMENTS

| | | | |
|---|---|---|---|
| 4,085,139 | 4/1978 | Nelson | 564/346 |
| 4,599,353 | 7/1986 | Bito | 514/530 |
| 4,883,819 | 11/1989 | Bito | 514/573 |
| 4,927,846 | 5/1990 | Gluchowski | 514/913 X |
| 4,952,581 | 8/1990 | Bito et al. | 514/913 X |
| 4,994,274 | 2/1991 | Chan et al. | 514/530 X |
| 5,001,153 | 3/1991 | Ueno et al. | 514/530 |
| 5,011,856 | 4/1991 | Woodward | 514/530 X |

FOREIGN PATENT DOCUMENTS

| | | |
|---|---|---|
| 0242580 | 10/1987 | European Pat. Off. . |
| 0253094 | 1/1988 | European Pat. Off. . |
| 2336924 | 7/1977 | France . |
| WO9119490 | 12/1991 | PCT Int'l Appl. . |

OTHER PUBLICATIONS

Nelson et al. "2-(aminomethyl)-2-decarboxyprostaglandin F2x Type Analogs", Prostaglandins 17(3), 1979, 441-449.

Primary Examiner—Thurman K. Page
Attorney, Agent, or Firm—Robert J. Baran; Howard R. Lambert; Martin A. Voet

[57] ABSTRACT

The present invention concerns 2-decarboxyl-2-aminoalkyl derivatives of naturally occurring and synthetic prostaglandins, N-substituted derivatives, ester prodrugs and homologues of such compounds that are potent ocular hypotensives, and are particularly suitable for the management of glaucoma.

7 Claims, 1 Drawing Sheet

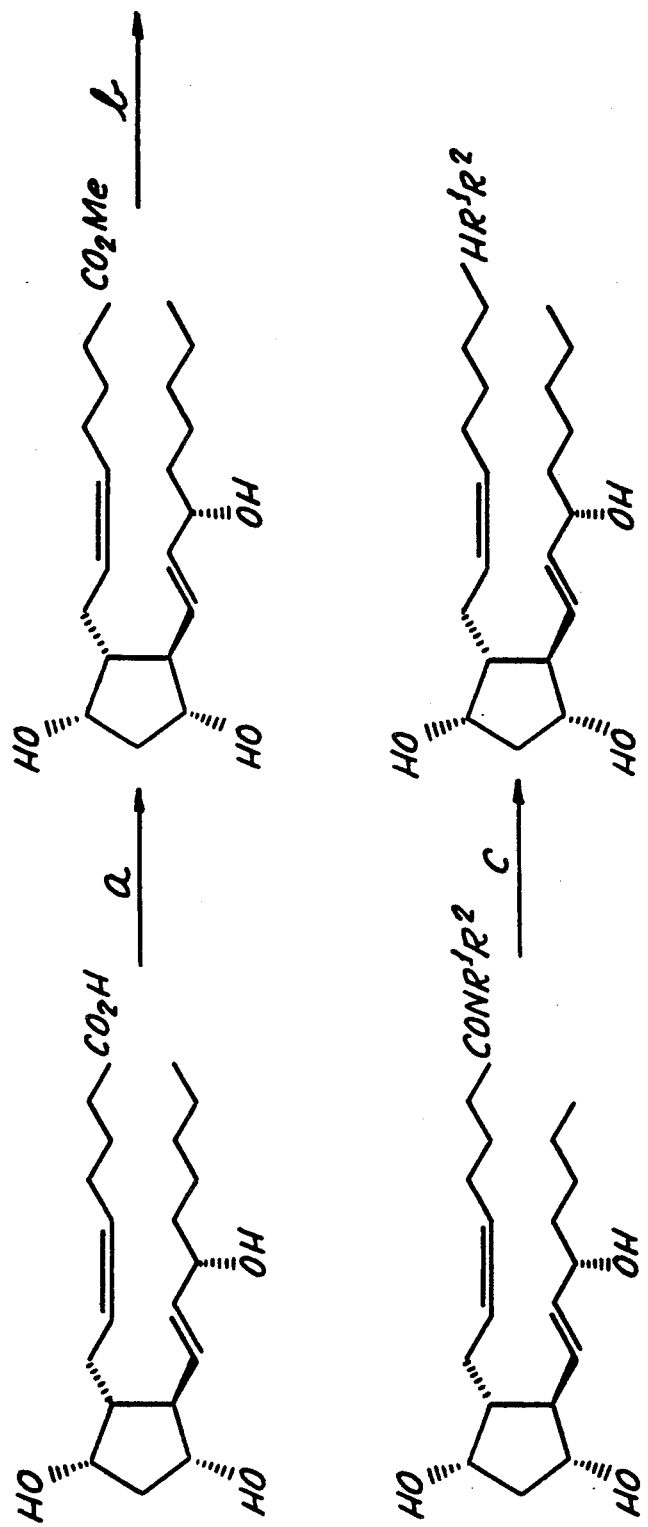

2-DECARBOXYL-2-AMINOALKYL-PROSTA-GLANDINS AS OCULAR HYPOTENSIVES

FIELD OF THE INVENTION

The present invention relates to 2-decarboxyl-2-aminoalkyl prostaglandin derivatives. More particularly, the present invention concerns 2-decarboxyl-2-aminoalkyl derivatives of naturally occurring and synthetic prostaglandins, N-substituted derivatives, ester prodrugs and homologues of such compounds that are potent ocular hypotensives, and are particularly suitable for the management of glaucoma.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical $\beta$-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which has the following structural formula:

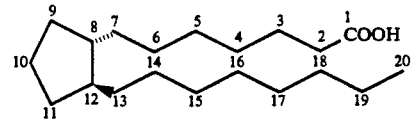

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ (PGE$_1$), prostaglandin $E_2$ (PGE$_2$)], and on the configuration of the substituents on the alicyclic ring indicated by $\alpha$ or $\beta$ [e.g. prostaglandin $F_{2\alpha}$ (PGF$_{2\alpha}$)].

Prostaglandins were earlier regarded as potent ocular hypertensives, however, evidence accumulated in the last decade shows that some protaglandins are highly effective ocular hypotensive agents, and are ideally suited for the long-term medical management of glaucoma (see, for example, Bito, L. Z. *Biological Protection With Prostaglandins* Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505). Such prostaglandins include PGF$_{2\alpha}$, PGF$_{1\alpha}$, PGE$_2$, and certain lipid-soluble esters, such as $C_1$ to $C_2$ alkyl esters, e.g. 1-isopropyl ester, of such compounds.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28(suppl), 284 (1987)].

The isopropyl ester of PGF$_{2\alpha}$ has been shown to have significantly greater hypotensive potency than the parent compound, presumably as a result of its more effective penetration through the cornea. In 1987 this compound was described as "the most potent ocular hypotensive agent ever reported" [see, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular PGF$_{2\alpha}$ and its prodrugs, e.g. its 1-isopropyl ester, in humans. The clinical potentials of prostaglandins in the management of conditions associated with increased ocular pressure, e.g. glaucoma are greatly limited by these side effects.

In a series of co-pending U.S. patent applications assigned to Allergan, Inc. prostaglandin esters with increased ocular hypotensive activity accompanied with no or substantially reduced side-effects are disclosed. The co-pending U.S. Ser. No. 386,835 (filed 27 Jul. 1989), relates to certain 11-acyl-prostaglandins, such as 11-pivaloyl, 11-acetyl, 11-isobutyryl, 11-valeryl, and 11-isovaleryl PGF$_{2\alpha}$. Intraocular pressure reducing prostaglandins are disclosed in the co-pending application U.S. Ser. No. 357,394 (filed 25 May 1989). Similarly, 11,15- 9,15- and 9,11-diesters of prostaglandins, for example 11,15-dipivaloyl PGF$_{2\alpha}$ are known to have ocular hypotensive activity. See the co-pending patent applications U.S. Ser. Nos. 385,645, 386,312 and 386,834

(all filed 27 Jul. 1989). PGF 1-alcohols and their use as ocular hypotensives are disclosed in co-pending patent application U.S. Ser. No. (filed 14 Jun. 1990). The disclosures of all of these patent applications are hereby expressly incorporated by reference.

Certain 2-decarboxyl-2-aminomethyl PG derivatives are known in the art.

N-dimethylamino-2-decarboxy $PGF_{2\alpha}$ was, for example, described by Fitzpatrick et al., in *NATO Adv. Study Inst. Ser.*, Ser. A, A36, 283-289 (1981). The compound attenuated $PGF_{2\alpha}$-induced increases in lobular arterial pressure of perfused canine lung in situ.

2-decarboxyl-2-aminomethyl $PGF_{2\alpha}$-type analogues were disclosed by Nelson et al., in *Prostaglandins* 17(3), 441-449 (1979). According to this publication, the disclosed analogues closely resemble the parent $PGF_{2\alpha}$ compounds as antifertility agents in the hamster.

2-decarboxyl-2-aminomethyl-5,9-alpha-prostacyclin analogues, especially of the F series, are disclosed in the Belgian Patent Application No. 860,278, claiming the priority of U.S. Ser. No. 788,143, filed 19 Apr. 1977.

Maddox et al., *Nature* 273, 549-552 (1978) tested the antagonistic behaviour of fourteen amide and 1-amino derivatives of prostaglandin F compounds, using the response of gerbil colon to $PGF_{2\alpha}$.

2-decarboxyl-2-aminomethyl PGE and PGD analogues are disclosed in the U.S. Pat. No. 4,085,139.

There is no mention in any of the foregoing publications of the ocular hypotensive activity of 1-decarboxy-1-aminomethyl prostaglandin derivatives.

SUMMARY OF THE INVENTION

We have surprisingly found that 2-decarboxyl-2-aminomethyl derivatives of prostaglandins are distinctly more potent than their parent compounds. Also, especially in lower doses, they cause significantly lower ocular surface hyperemia than the parent compounds.

Accordingly, the present invention concerns a method of treating ocular hypertension which comprises applying to the eye an amount sufficient to treat ocular hypertension of a compound of formula (I)

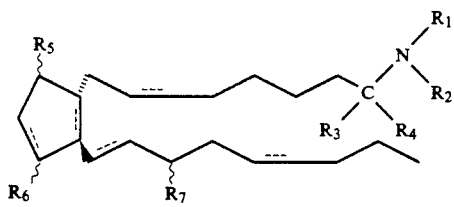

wherein the wavy line attachments indicate either alpha ($\alpha$) or beta ($\beta$) configuration; hatched lines indicate $\alpha$ configuration, solid triangles are used to indicate $\beta$ configuration; the dashed bonds represent a single bond or a double bond which can be in the cis or trans configuration; $R_1$ and $R_2$ independently are hydrogen, an aliphatic hydrocarbon group having from 1 to about 6 carbon atoms, or a —CO(Y) group, wherein Y is an aliphatic hydrocarbon group having from 1 to about 6 carbon atoms; $R_3$ and $R_4$ independently are hydrogen, or an aliphatic hydrocarbon group having from 1 to about 6 carbon atoms; one of $R_5$ and $R_6$ is $=$O, —OH or an —O(CO)$R_8$ group, and the other one is —OH or an —O(CO)$R_8$ group or $R_5$ is $=$O and $R_6$ is H; $R_7$ is —OH or —O(CO)$R_8$, wherein $R_8$ is a saturated or unsaturated acyclic hydrocarbon group having from 1 to about 20 carbon atoms, or —(CH$_2$)$_n$R$_9$ wherein n is 0-10, and $R_9$ is an aliphatic ring from about 3 to about 7 carbon atoms, or an aromatic or heteroaromatic ring; or a pharmaceutically acceptable salt thereof.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application.

In a still further aspect, the present invention relates to a pharmaceutical product, comprising a container adapted to dispense its contents in metered form; and an ophthalmic solution therein, as hereinabove defined.

BRIEF DESCRIPTION OF THE DRAWINGS

The sole FIGURE represents a typical synthesis route in the preparation of the compounds of the present invention.

DETAILED DESCRIPTION OF THE INVENTION

The present invention relates to the use of 2-decarboxyl-2-aminoalkyl prostaglandin compounds, and their derivatives and analogues as ocular hypotensives. The prostaglandin derivatives used in accordance with the present invention are encompassed by the structural formula (I)

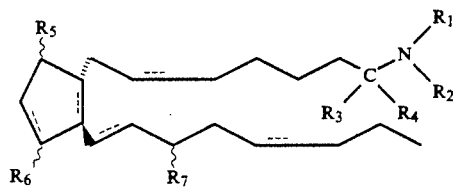

wherein the substituents and symbols are as hereinabove defined.

The above formula includes 2-decarboxyl-2-aminoalkyl derivatives of prostaglandins of the F, D, E, A and B series. A preferred group of the compounds of the present invention is encompassed by the following formula (II)

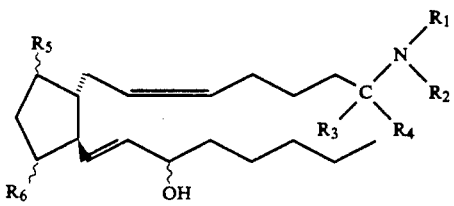

wherein $R_5/R_6$ is —OH/—OH, $=$O/—OH, —OH/$=$O and the esters of these compounds. This definition includes PGF, PGE, and PGD derivatives.

Particularly preferred are the $PGF_{2\alpha}$ derivatives of the formula (III)

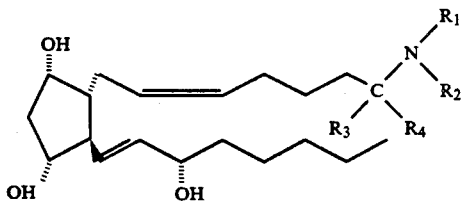

and their 9- and/or 11- and/or 15-esters.

In all of the above formulae, as well as in those provided hereinafter, the dotted lines on bonds between carbons 5 and 6 (C-5), between carbons 13 and 14 (C-13), between carbons 8 and 12 (C-8), between carbons 10 and 11 (C-10) and between carbons 17 and 18 (C-17) indicate a single or a double bond which can be in the cis or trans configuration. If two solid lines are used that indicates a specific configuration for that double bond. Hatched lines at positions C-9, C-11 and C-15 indicate the α configuration. If one were to draw the β configuration, a solid triangular line would be used.

The naturally occurring stereochemistry of PGF$_{2\alpha}$ includes the C-9, C-11, and C-15 hydroxyl groups in the α configuration. In the compounds used in accorance with the present invention, however, prostaglandins having the C-9 or C-11 or C-15 substituents in β configuration are also contemplated. As hereinabove mentioned, in all formulas provided herein broken line attachments to the cyclopentane ring indicate substituents in the α configuration. Thickened solid line attachments to the cyclopentane ring indicate substituents in the β configuration. For instance, 9β-PGF compounds have the same structure as PGF$_\alpha$ compounds, except that the hydroxyl at the C-9 position is in the β configuration. Also, the broken line attachment of the hydroxyl group or other substituent to the C-11 and C-15 carbon atoms signifies the α configuration; therefore, compounds with the epi configuration for the hydroxyl group at C-15 are designated by using 15β and if there is no indication of the β configuration, the configuration is assumed α.

In the substituent definitions, the "aliphatic hydrocarbon groups" have from 1 to about 6, most preferably 1 to about 4 carbon atoms. The aliphatic hydrocarbon groups may be straight or branched chained, saturated or unsaturated, such as straight or branched chained alkyl, alkenyl, alkynyl groups. Typical representatives of the alkyl groups include, for example, methyl, ethyl, n- and isopropyl, n-, sec-, iso- and tert-butyl, n- and isopentyl, n- and neohexyl, etc. groups. Typical alkenyl and alkynyl groups are vinyl, allyl, propenyl, ethynyl and propargyl.

The definition of $R_8$ may include a cyclic component, —(CH$_2$)$_n$R$_9$, wherein n is 0–10, R$_9$ is an aliphatic ring from about 3 to about 7 carbon atoms, or an aromatic or heteroaromatic ring. The "aliphatic ring" may be saturated or unsaturated, and preferably is a saturated ring having 3-7 carbon atoms, inclusive. As an aromatic ring, R$_9$ preferably is phenyl, and the heteroaromatic rings have oxygen, nitrogen or sulfur as a heteroatom. Preferably n is 0–4.

The most preferred compounds are those PGF$_{2\alpha}$ derivatives in which both R$_1$ and R$_2$ are hydrogen or one of R$_1$ and R$_2$ is hydrogen, and the other one is an aliphatic hydrocarbon group having from 1 to 6, preferably 1 to 4 carbon atoms. Particularly preferred are the compounds in which R$_3$ and R$_4$ both represent hydrogen.

Especially preferred compounds of formula (I) are: 2-decarboxyl-2-dimethylaminomethyl PGF$_{2\alpha}$, and 2-decarboxyl-2-aminomethyl PGF$_{2\alpha}$.

The compounds of the present invention can be prepared by methods known in the art. A typical synthesis route is illustrated in Reaction Scheme I, wherein step a) is typically performed with CH$_2$N$_2$ in ethanol/methanol; in step b) a suitable amine or its hydrochloride is used as reactant, and the reaction is performed in a sealed tube, at about 70° C.; and step c) is accomplished in excess LiAlH$_4$/THF, at about 25° C.

A pharmaceutically acceptable salt is any salt which retains the activity of the parent compound and does not impart any deleterious or undesirable effect on the subject to whom it is administered and in the context in which it is administered. Of particular interest are the acid addition salts of the amine compounds of the present invention.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The invention is further illustrated by the following non-limiting Examples.

EXAMPLE 1

2-Decarboxyl-2-dimethylaminomethyl $PGF_{2\alpha}$ $PGF_{2\alpha}$ methyl ester (47.6 mg, 0.129 mmol) was placed in a pressure flask. About 2 ml of dimethylamine was condensed into the flask by using a dry ice-acetone bath and dimethylamine hydrochloride (78 mg) was added. The flask was sealed and heated at 75° C. for 44 h. The flask was cooled to $-78°$ C. and opened. Excess dimethylamine was swept away by a stream of argon at 25° C. The residue was partitioned between saturated ammonium chloride and ethyl acetate. After extracting with ethyl acetate, the organic layer was washed with water and brine and dried over magnesium sulfate. Removal of solvent gave an oil which was purified by means of flash chromatography on silica gel using 14:1 methylene chloride/methanol as eluent to give 38 mg pure $PGF_{2\alpha}$ dimethylamide. IR: 1630 cm$^{-1}$.

To a solution of $PGF_{2\alpha}$ dimethylamide (27 mg, 0.07 mmol) in anhydrous tetrahydrofuran (1.0 ml) was added a solution of lithium aluminum hydride (1.0M, 0.28 ml, 0.28 mmol) at 0° C. The solution was allowed to warm up to room temperature and stirred for 18 h. The reaction was quenched with a few drops of methanol and concentrated under vacuum. The residue was taken up in ethyl acetate (5 ml), washed with water and brine and dried over magnesium sulfate. Evaporation of solvent gave a crude product which was purified by preparative thin layer chromatography (silica gel plates, ammonia saturated methanol/methylene chloride 1:9) to give 8.5 mg of 2-decarboxyl-2-dimethylaminomethyl $PGF_{2\alpha}$.

$^1$H NMR (300 MHz, CDCl$_3$): $\delta$5.53 (2H, ABX, $J_{AB}=15.3$, $J_{AX}=6$, $J_{BX}=7.3$ Hz), 538 (2H, complex AB), 4.16 (1H, t, J=3.9 Hz), 4.06 (1H, q, J=6.2 Hz), 3.96 (1H, m), 1.7-2.4 (12H, m), 2.21 (6H, s), 1.79 (1H, br d, J=15 Hz), 1.2-1.65 (12H, m), 0.88 PPM (3H, t, J=6.7 Hz); $^{13}$C NMR (75 MHz, CDCl$_3$): $\delta$135.30, 132.75, 130.78, 128.77, 78.18, 72.86, 72.60, 59.18, 55.84, 50.59, 45.10, 42.94, 37.14, 31.58, 26.88, 26.69, 26.59, 25.30, 25.05, 22.41, 13.80 ppm;

MS (CI): m/z 584 (M+, 100%), 512 (8%), 90 (20%);

HRMS: calculated for C$_{31}$H$_{66}$O$_3$NSi$_3$:584.4351, found: 584.4343.

EXAMPLE 2

2-Decarboxyl-2-aminomethyl $PGF_{2\alpha}$

In a similar manner, 2-decarboxyl-2-aminomethyl $PGF_{2\alpha}$ was prepared from $PGF_{2\alpha}$, ammonia and ammonium chloride.

$^1$H NMR (300 MHz, CDCl$_3$): $\delta$5.48 (2H, ABX, $J_{AB}=15$, $J_{AX}=6$, $J_{BX}=8$ Hz), 5.27-5.4 (2H, m), 4.10 (1H, t, J=4 Hz), 4.02 (1H, q, J=6 Hz), 3.91 (1H, m), 3.2-3.4 (5H, br s), 2.71 (2H, t, J=7 Hz, CH$_2$—NH$_2$), 1.2-2.4 (20H, m), 0.84 ppm (3h, distorted t, J~6 Hz);

$^{13}$C NMR (75 MHz, CDCl$_3$): $\delta$ 135.60, 132.77, 130.46, 128.90, 77.84, 72.80, 72.46, 55.68, 50.40, 42.96, 40.71, 37.12, 31.60, 30.90, 26.39, 26.16, 25.27, 25.08, 22.43, 13.81 ppm;

MS (CI, NH$_3$, TMS derivative): m/z 628 (M+1, 100%), 200 (16), 145 (22), 90 (77);

HRMS (CI, TMS derivative): calculated for C$_{32}$H$_{70}$O$_3$NSi$_4$: 628.4433, found 628.4413.

EXAMPLE 3

Intraocular Pressure Reducing Activity

Experimental quantities of the test compounds were prepared in an ophthalmic formulation containing 0.1% polysorbate (Tween 80) 10 mM TRIS. One eye of each experimental animal was treated by applying one 25 $\mu$l drop of the drug formulation to the ocular surface, the contralateral eye received 25 $\mu$l of vehicle as a control. Intraocular pressure was measured by applanation pneumatonometry immediately before drug administration and at subsequent, predetermined times thereafter. New Zealand albino/dutch belted cross rabbits were employed as experimental animals.

Ocular surface hyperemia was assessed by observation at predetermined times after drug administration and is described as either present or absent.

The data obtained are shown in Tables 1 and 2.

TABLE I

| PROSTANOID | (DOSE %) | 0 | 0.5 | 1.0 | 2.0 | 3.0 | 4.0 | 6.0 | 8.0 |
|---|---|---|---|---|---|---|---|---|---|
| | | EFFECT ON INTRAOCULAR PRESSURE (mmHg) AT PREDETERMINED TIMES POST-ADMINISTRATION | | | | | | | |
| $PGF_{2\alpha}$-2-N(CH$_3$)$_2$ | 0.01% | $-2.9^*$ | $-2.2$ | $-0.6$ | $-1.8$ | $-3.3^{**}$ | $+0.2$ | — | |
| $PGF_{2\alpha}$-2-N(CH$_3$)$_2$ | 0.1% | $+2.0$ | $+0.4$ | $-3.0^*$ | $-6.6^{}$ | $-7.3^{}$ | $-4.1^{**}$ | | |
| $PGF_{2\alpha}$-2-N(CH$_3$)$_2$ | 1.0% | — | $+10.9^{}$ | $+7.3^{}$ | $+0.4$ | $-3.4$ | $-8.3^{}$ | $-10.1^{}$ | |
| | | % ANIMALS EXHIBITING OCULAR SURFACE HYPEREMIA | | | | | | | |
| $PGF_{2\alpha}$-2-N(CH$_3$)$_2$ | 0.01% | 87 | 87 | 87 | — | 13 | 0 | — | |

TABLE I-continued

| PROSTANOID | (DOSE %) | 0 | 0.5 | 1.0 | 2.0 | 3.0 | 4.0 | 6.0 | 8.0 |
|---|---|---|---|---|---|---|---|---|---|
| PGF$_{2\alpha}$-2-N(CH$_3$)$_2$ | 0.1% | 100 | 100 | 100 | 87 | 87 | 63 | — | |
| PGF$_{2\alpha}$-2-N(CH$_3$)$_2$ | 1.0% | — | 100 | 100 | 100 | 100 | 83 | 67 | |

TABLE II

| PROSTANOID | (DOSE %) | 0 | 0.5 | 1.0 | 2.0 | 3.0 | 4.0 | 6.0 | 8.0 |
|---|---|---|---|---|---|---|---|---|---|
| | | EFFECT ON INTRAOCULAR PRESSURE (mmHg) AT PREDETERMINED TIMES POST-ADMINISTRATION | | | | | | | |
| PGF$_{2\alpha}$-2-NH$_2$ | 0.01% | | −1.7* | −3.8** | −2.7** | −2.9* | −3.8** | −1.8** | |
| PGF$_{2\alpha}$-2-NH$_2$ | 0.1% | | −1.4 | −0.4 | −1.75 | −2.6* | −3.4 | −4.9** | |
| PGF$_{2\alpha}$-2-NH$_2$ | 1.0% | | — | +11.9* | +12.4** | +9.5* | +6.6* | −3.7* | |
| | | % ANIMALS EXHIBITING OCULAR SURFACE HYPEREMIA | | | | | | | |
| PGF$_{2\alpha}$-2-NH$_2$ | 0.01% | | 0 | 66 | 33 | 17 | 17 | 17 | |
| PGF$_{2\alpha}$-2-NH$_2$ | 0.1% | | 100 | 100 | 100 | 100 | 100 | 87.5 | |
| PGF$_{2\alpha}$-2-NH$_2$ | 1.0% | | 100 | 100 | 100 | 100 | 100 | 100 | |

The foregoing description details specific methods and compositions that can be employed to practice the present invention, and represents the best mode contemplated. However, it is apparent from one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

We claim:

1. A method of treating ocular hypertension which comprises applying to the eye an amount sufficient to treat ocular hypertension of a compound of formula (I)

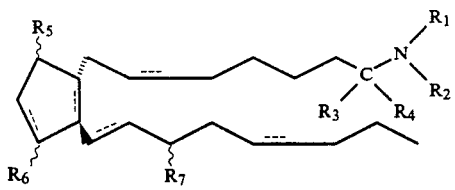

wherein the wavy line attachments indicate either alpha ($\alpha$) or beta ($\beta$) configuration; hatched lines indicate $\alpha$ configuration, solid triangles are used to indicate $\beta$ configuration; the dashed bonds represent a single bond or a double bond which can be in the cis or trans configuration; $R_1$ and $R_2$ independently are hydrogen, an aliphatic hydrocarbon group having from 1 to about 6 carbon atoms, or a —CO(Y) group, wherein Y is an aliphatic hydrocarbon group having from 1 to about 6 carbon atoms; $R_3$ and $R_4$ independently are hydrogen, or an aliphatic hydrocarbon group having from 1 to about 6 carbon atoms; one of $R_5$ and $R_6$ is =O, —OH or an —O(CO)R$_8$ group, and the other one is —OH or an —O(CO)R$_8$ group or $R_5$ is =O and $R_6$ is H; $R_7$ is —OH or —O(CO)R$_8$, wherein R$_8$ is a saturated or unsaturated acyclic hydrocarbon group having from 1 to about 20 carbon atoms, or —(CH$_2$)$_n$R$_9$ wherein n is 0–10, and R$_9$ is an aliphatic ring from about 3 to about 7 carbon atoms, or an aromatic or heteroaromatic ring; or a pharmaceutically acceptable salt thereof.

2. The method of claim 1 wherein said compound of formula (I) is selected from the group consisting of 2-decarboxyl-aminoalkyl derivatives of naturally occurring prostaglandins of the D, E and F series.

3. The method of claim 1 wherein said compound is a PG derivative of the formula (II)

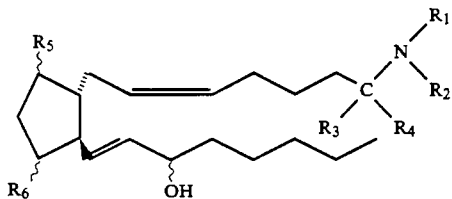

wherein $R_1$, $R_2$, $R_3$ and $R_4$ are as defined in claim 1 and $R_5/R_6$ is —OH/—OH, =O/—OH, —OH/=O, or an —O(CO)R$_8$ ester thereof.

4. The method of claim 3 wherein said compound is a PGF$_{2\alpha}$ derivative of the formula (III)

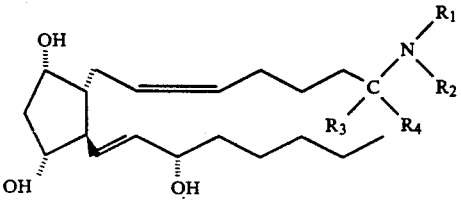

wherein $R_1$, $R_2$, $R_3$ and $R_4$ are as defined in claim 1.

5. The method of claim 4 wherein in the formula both $R_1$ and $R_2$ are hydrogen or one of $R_1$ and $R_2$ is hydrogen, and the other one is an aliphatic hydrocarbon group having from 1 to 6 carbon atoms, and $R_3$ and $R_4$ are as defined in claim 1.

6. The method of claim 5, wherein in the formula $R_3$ and $R_4$ both are hydrogen.

7. The method of claim 6 wherein said compound of formula (I) is selected from the group consisting of 2-decarboxyl-2-aminomethyl $PGF_{2\alpha}$, and 2-decarboxyl-2-dimethylaminomethyl $PGF_{2\alpha}$.

* * * * *